United States Patent [19]
Griat

[11] Patent Number: 6,001,379
[45] Date of Patent: Dec. 14, 1999

[54] STABLE ACIDIC OIL-IN- WATER TYPE EMULSIONS AND COMPOSITIONS CONTAINING THEM

[75] Inventor: Jacqueline Griat, Ablon, France

[73] Assignee: L'Oreal, Paris, France

[21] Appl. No.: 09/157,517

[22] Filed: Sep. 21, 1998

Related U.S. Application Data

[60] Continuation of application No. 08/621,344, Mar. 25, 1996, Pat. No. 5,863,545, which is a division of application No. 08/305,912, Sep. 5, 1994, Pat. No. 5,531,993.

[30] Foreign Application Priority Data

Sep. 15, 1993 [FR] France ................................. 93 10966

[51] Int. Cl.$^6$ ................................. A61K 7/00; A61K 7/48
[52] U.S. Cl. ................... 424/401; 424/78.03; 514/937; 514/938; 514/970
[58] Field of Search ............................. 424/78.03, 401; 514/937, 938, 970

[56] References Cited

U.S. PATENT DOCUMENTS

| | | |
|---|---|---|
| 4,059,552 | 11/1977 | Zweigle . |
| 4,459,369 | 7/1984 | Yamasaki ................. 526/200 |
| 4,459,396 | 7/1984 | Yamasaki ................. 526/200 |
| 4,710,374 | 12/1987 | Grollier . |
| 4,767,750 | 8/1988 | Jacquet . |
| 5,262,407 | 11/1993 | Leveque . |
| 5,292,800 | 3/1994 | Moench . |
| 5,422,112 | 6/1995 | Williams . |
| 5,531,993 | 7/1996 | Griat . |
| 5,605,894 | 2/1997 | Blank . |

FOREIGN PATENT DOCUMENTS

| | | |
|---|---|---|
| 2119626 | 4/1993 | Canada . |
| 2132144 | 12/1997 | Canada . |
| 0503853A2 | 9/1992 | European Pat. Off. . |
| 0 642 718 A1 | 3/1995 | European Pat. Off. . |
| 2681245 | 3/1993 | France . |
| 2709982 | 3/1995 | France . |
| 5-4913 | 1/1993 | Japan . |
| 9686301 | 2/1993 | Japan . |
| 2693116 | 3/1993 | Japan . |
| 101509 | 3/1995 | Japan . |
| 220231/94 | 7/1997 | Japan . |
| 2 257 152 | 1/1993 | United Kingdom . |
| 2257152 | 1/1993 | United Kingdom . |
| WO 93/07856 | 4/1993 | WIPO . |

*Primary Examiner*—Thurman K. Page
*Assistant Examiner*—Alysia Berman
*Attorney, Agent, or Firm*—Oblon, Spivak, McClelland, Maier & Neustadt, P.C.

[57] ABSTRACT

Oil-in-water type emulsions having a pH below or equal to 3.5, especially a pH below or equal to 3, and comprising as a stabilizing agent a substantially water-soluble crosslinked anionic copolymer consisting of units derived from the reaction between (i) acrylamide, (ii) 2-acrylamido-2-methylpropanesulfonic acid and (iii) at least one compound possessing multiple olefinic unsaturation (crosslinking agent), in which the compound possessing multiple olefinic unsaturation is present in the copolymer at a concentration of between 0.06 and 1 mmol per mole of the collective monomer units, are stable.

31 Claims, No Drawings

STABLE ACIDIC OIL-IN-WATER TYPE EMULSIONS AND COMPOSITIONS CONTAINING THEM

This application is a continuation of application Ser. No. 08/621,344 filed Mar. 25, 1996, now U.S. Pat. No. 5,863,545, which is a divisional of application Ser. No. 08/305,912, filed Sep. 5, 1994, now U.S. Pat. No. 5,531,993

BACKGROUND OF THE INVENTION

1. Field of the Invention

The present invention relates to new oil-in-water (O/W) type emulsions, that is to say emulsions in which the continuous dispersing phase is aqueous and the discontinuous disperse phase is oily, which are both markedly acidic and completely stable, as well as to cosmetic and/or dermatological and/or pharmaceutical compositions containing such emulsions. The present invention also relates to the use of a specific polymer for the purpose of stabilizing O/W type emulsions or compositions based on such emulsions possessing markedly acidic pH values.

2. Discussion of the Background

For various reasons associated especially with the fact that they are very agreeable to use (possessing gentleness, emollience and the like), oil-in-water type emulsions are nowadays widely employed in the field of cosmetic or pharmaceutical compositions intended for topical use (skin, hair). Besides the traditional emulsifying agents which are usually needed for their preparation, these emulsions generally contain, both in the aqueous phase and in the oily phase (also known as fatty phase), cosmetically or therapeutically active principles which are required to be released on application of the composition containing the emulsion to the body.

Some oil-in-water type emulsions, while containing emulsifying agents (or surfactants) as mentioned above, are of low chemical stability, especially when these emulsions are highly concentrated with respect to the fatty phase and/or when they contain agents which are not compatible with the remainder of the constituents forming the emulsion. This lack or absence of stability manifests itself in practice in a separation (by settling) of the aqueous and oily phases of the emulsion, it being possible for this separation to be more or less gradual and/or more or less complete depending on the case.

To avoid this undesirable phenomenon, it is often necessary to resort to so-called thickening agents, which are then introduced into the emulsion and whose primary function is to create, within the aqueous phase, a gelatinous matrix serving to immobilize (or "confine") the particles (or globules) of the fatty phase in its three-dimensional network, thus providing for a kind of stabilization or mechanical maintenance of the whole of the emulsion. This approach, though effective, nevertheless substantially modifies the rheological properties of the initial emulsion, and this is not always compatible with some of the applications envisaged for the final composition.

The above stabilization technique is unfortunately not generally applicable, that is to say it is not suitable for all oil-in-water type emulsions for which stabilization might be necessary or desirable. Such is the case with emulsions which possess markedly acidic pH values, especially pH values below or equal to 3.5, and still more especially below or equal to 3, and which are intrinsically of low chemical stability. Such acidic emulsions may be encountered, in particular, when it is desired to obtain cosmetic and/or pharmaceutical compositions containing acidic active agents, such as, for example, hydroxy acids having exfoliative/moisturizing properties, acidic compositions for which there is currently a strong need.

In effect, when it is desired to stabilize such acidic emulsions (i.e. having pH values below or equal to 3.5) in a conventional manner by means of the standard thickening agents, it is found not only that these thickening agents do not exert their known primary thickening function therein, but also that they produce a destabilizing and destructive effect contrary to the desired effect, leading to a separation of the aqueous and oily phases of the initial emulsion. As far as the Applicant is aware, there is at present no simple, effective, and reliable method enabling acidic and stable oil-in-water type emulsions to be prepared and obtained.

SUMMARY OF THE INVENTION

Accordingly, it is one object of the present invention to provide novel stable acidic oil-in-water emulsions.

It is another object of the present invention to provide oil-in-water emulsions which have a pH of less than or equal to 3.5 and which are stable.

It is another object of the present invention to provide oil-in-water emulsions which have a pH of less than or equal to 3 and which are stable.

It is another object of the present invention to provide novel compositions containing such an emulsion.

It is another object of the present invention to provide a novel method for stabilizing oil-in-water emulsions which are acidic.

It is another object of the present invention to provide a method for stabilizing oil-in-water emulsions which have a pH of less than or equal to 3.5.

It is another object of the present invention to provide a method for stabilizing oil-in-water emulsions which have a pH of less than or equal to 3.

These and other objects, which will become apparent during the following detailed description, have been achieved by the inventor's discovery that unexpectedly and surprisingly, by employing a specific polymer which is introduced into an oil-in-water type emulsion initially possessing a pH below or equal to 3.5 and in an unstable state, it is possible to obtain a final emulsion which is also of the oil-in-water type, having the same pH, but which is completely stable.

This discovery has made the present invention possible.

According to one of the objects of the present invention, stable oil-in-water type emulsions having a pH below or equal to 3.5, especially a pH below or equal to 3, are hence now provided. Specifically, the present emulsions comprise as a stabilizing agent a substantially water-soluble crosslinked anionic copolymer consisting of units derived from the reaction between (i) acrylamide (monomer 1), (ii) 2-acrylamido-2-methylpropanesulfonic acid (monomer 2, hereinafter designated AMPS for convenience) and (iii) at least one compound possessing multiple olefinic unsaturation (monomer 3, here constituting the crosslinking agent), in which the compound possessing multiple olefinic unsaturation is present in the copolymer at a concentration of between 0.06 and 1 mmol per mole based on the total monomer units.

Another aspect of the present invention is the use of a polymer as defined above for stabilizing oil-in-water type emulsions possessing a pH below or equal to 3.5, especially below or equal to 3, as well as the stabilization process resulting therefrom. According to the present invention, the present method simply involves introducing the copolymer into the initial acidic emulsion to be stabilized.

It will be noted already that the present invention is of very general scope, that is to say the present method is appropriate for the stabilization of any acidic emulsion (having a pH below or equal to 3.5) of the oil-in-water type, already known per se or otherwise, the composition of the latter not assuming, in fact, any critical character.

Lastly, another aspect of the present invention consists of the various compositions, cosmetic, dermatological, and pharmaceutical, prepared and obtained from the emulsions according to the invention. In this connection, the present invention is especially well suited to the preparation of compositions which take the form of emulsions of the above type and which contain cosmetic and/or therapeutic active agents possessing markedly acid character.

DETAILED DESCRIPTION OF THE PREFERRED EMBODIMENTS

The crosslinked anionic copolymers used as stabilizing agents in the context of the present invention are products already known per se, and their preparation has been described, in particular, in European Patent Application EP-A-0,503,853, the content of which is incorporated herein in its entirety by reference. It should be noted here that the above-mentioned document does not relate in any way to, and neither describes nor provides useful teaching regarding, the solving of the very special problem of the stabilization of strongly acidic oil-in-water type emulsions.

The above copolymers may thus be obtained in a conventional manner according to the so-called emulsion polymerization technique, from the three different comonomers.

The monomer possessing multiple olefinic unsaturation used as a crosslinking agent for the preparation of the copolymers according to the invention is preferably chosen from the group consisting of methylenebisacrylamide, allylsucrose, and pentaerythritol. Still more preferably, methylenebisacrylamide is employed.

The ratio, expressed in mol %, of acrylamide to AMPS is generally between 85:15 and 15:85, preferably between 70:30 and 30:70, still more preferably between 65:35 and 35:65 and even more especially between 60:40 and 40:60. In addition, the AMPS is generally at least partially neutralized in the form of a salt, for example with sodium hydroxide, with potassium hydroxide or with a low molecular weight amine such as triethanolamine, or mixtures thereof. Preferably, the compound possessing multiple olefinic unsaturation is present in an amount of 0.08 to 0.7 mmole/mole of the total monomer units. Suitably, the copolymer will have a viscosity average molecular weight of 500,000 to 10,000,000, preferably 500,000 to 5,000,000.

An especially preferred crosslinked copolymer in the context of the present invention corresponds to the one prepared in Example 1 of European Patent Application EP-A-0,503,853 cited above, and which then takes the form of a water-in-oil reverse emulsion. More specifically, this copolymer consists of 60 molt of acrylamide and 40 molt of AMPS sodium salt, and it is crosslinked with methylenebisacrylamide in the proportion of 0.22 mmol per mole of the total monomer mixture. The final water-in-oil reverse emulsion contains, preferably, approximately 40% by weight of the crosslinked copolymer as defined above and on the order of 4% by weight of an ethoxylated fatty alcohol having an HLB of approximately 12.5.

The acidic oil-in-water type emulsions according to the present invention generally contain the crosslinked copolymer as defined above in a weight amount which can range from 0.01 to 5%, based on the total weight of the emulsion, and preferably between 0.1 and 3%, again based on to the total weight of the emulsion. It will be noted that the crosslinked copolymer serving as stabilizing agent for the emulsion is essentially present in the aqueous phase of the emulsion. In addition, depending on the amount of crosslinked copolymer present in the emulsion, it is possible to endow the emulsion with diverse and varied fluidities ranging, in particular, from that corresponding to a milk to that corresponding to a cream. Thus, unlike the products used in the prior techniques (stabilization of non-acidic or weakly acidic O/W emulsions by simple mechanical gelling of these latter), the crosslinked copolymer used in the present invention exerts a general stabilizing function on o/W emulsions of strongly acidic character; and when used at higher concentrations, the copolymer then exerts a dual function, namely both a stabilizing function and a function of thickening of strongly acidic O/W emulsions. Of course, either a single copolymer may be used or a mixture of two or more copolymers may be used.

In the emulsions according to the present invention, the oily phase advantageously represents from 2 to 35% by weight based on the total weight of the emulsion. Still more preferably, this proportion is from 5 to 30% by weight.

As stressed above, this oily or fatty phase can comprise any compound which is already generally known to be suitable for the production of oil-in-water type emulsions. In particular, these compounds may be chosen, alone or mixed, from the various fats, oils of vegetable, animal or mineral origin, natural or synthetic waxes, and the like.

Among oils which can participate in the composition of the fatty phase, there may be mentioned in particular:

mineral oils such as paraffin oil and liquid petrolatum;

oils of animal origin such as perhydrosqualene;

oils of vegetable origin such as sweet almond oil, avocado oil, castor oil, olive oil, jojoba oil, sesame oil, groundnut oil, grape-pip oil, rapeseed oil, copra oil, hazelnut oil, shea butter, palm oil, apricot-kernel oil, calophyllum oil, rice-bran oil, maize-germ oil, wheat-germ oil, soya-bean oil, sunflower oil, oenothera oil, safflower oil, passionflower oil, and rye oil;

synthetic oils such as purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, propylene glycol dicaprylate and esters derived from lanolic acid such as isopropyl lanolate, isocetyl lanolate and isoparaffins.

As other oils which are usable in the emulsions according to the invention, there may also be mentioned acetylglycerides, the octanoates and decanoates of alcohols and of polyhydric alcohols such as those of glycol and glycerol, the ricinoleates of alcohols and of polyhydric alcohols such as the cetyl compounds, fatty acid triglycerides such as caprylic/capric triglycerides, $C_{10}$–$C_{18}$ saturated fatty acid triglycerides, fluorinated and perfluorinated oils and lastly volatile or non-volatile silicone oils.

Naturally, the fatty phase can also contain one or more lipophilic cosmetic and/or therapeutic active agents, in particular those which are already used commonly in the production and obtaining of cosmetic and/or pharmaceutical compositions. These active agents can be, for example, anti-free-radical agents, ceramides, sunscreen agents such as 2-ethylhexyl para-methoxycinnamate and especially that marketed under the name "Parsol MCX" by the company GIVAUDAN, or 2-hydroxy-4-methoxybenzophenone and especially that sold under the trade name "Uvinul M40" by the company BASF, insect repellents such as n-butyl 3-(cetyl)ethylaminopropionate or caprylic acid N,N-diethylamide, slimming agents such as DL-α-tocopherol nicotinate, oily extract of ginseng (Panax ginseng), oily extract of English ivy (Hedera helix), oily extract of dry arnica (Arnica montana L) flowers and oily extract of seaweed (Fucus vesiculosus). It is self-evident that the above list of lipophilic active agents capable of comprising the fatty phase is in no way exhaustive.

The fatty phase can also contain, depending on the application envisaged, one or more lipophilic formulation additives such as preservatives, antioxidants, emollients, or perfumed oils.

The size of the particles of fatty phase within the dispersing aqueous phase can vary within wide limits, and it is chosen especially in accordance with the desired final application; it can thus either be submicronic (emulsoids), or range from 1 to several microns, for example.

In the emulsions according to the invention, the aqueous phase advantageously represents from 65 to 98% by weight based on the total weight of the emulsion. Still more preferably, this proportion is between 70 and 95% by weight.

In a conventional manner, this aqueous phase can consist of water or alternatively a mixture of water and water-soluble lower alcohols ($C_1$–$C_6$) and it can, in addition, contain cosmetic and/or therapeutic active agents which are also water-soluble.

Among the adjuvants capable of being contained in the aqueous phase, there may be mentioned, in particular:

water-soluble derivatives such as colorants and preservatives, active agents such as hyaluronic acid and its derivatives, or magnesium gluconate, trace elements, biological derivatives such as urea, pyrrolidonecarboxylic acid and its various salts, in particular its sodium salt, polyols such as propylene glycol, 1,3-butylene glycol, glycerol, polyglycerol, sorbitol, glucose and sucrose, salts such as magnesium sulfate and sodium chloride, clayey minerals which swell in an aqueous medium, such as saponite, hectorite and smectite, amino acids such as proline and hydroxyproline, proteins such as sulfonic keratins, collagen, elastin and DNA, emollients, antibacterial agents such as transthiolane-3,4-diol S-dioxide, water-soluble sunscreen agents such as 2-hydroxy-4-methoxybenzophenone-5-sulfonic acid, for example that marketed under the name "Uvinul MS40", by the company BASF, slimming agents such as caffeine, theobromine, theophylline, L-carnitine and dimethylaminoethyltheophylline hydrochloride, silicon derivatives of the methylsilanol theophyllineacetate alginate type, plant derivatives such as aqueous-glycolic extracts of English ivy, brown algae and fresh wild pansy, products for heavy legs such as Ginkgo biloba, sweet clover or ruscus.

The emulsions according to the invention can, in addition, contain, generally in the proportion of 0.3 to 20% by weight, based on the total weight of the emulsion, and preferably in the proportion of 0.5 to 10% by weight, surfactants or emulsifiers whose use may have been necessitated during the preparation of the initial emulsion not yet stabilized according to the present invention.

Such surfactants are all nonionic surfactants known to a person skilled in the art for producing an oil-in-water type emulsion in a traditional manner. As examples of suitable nonionic surfactants, there may be mentioned, in particular:

fatty acid esters of sorbitan, oxyethylenated or otherwise, such as sorbitan laurate, palmitate, stearate, oleate or tristearate, especially those sold under the name "Span" by the company ICI, and oxyethylenated compounds such as the polysorbates marketed under the name "Tween" by the company ICI.

fatty acid esters of polyethylene glycols, such as PEG-8 stearate, PEG-20 stearate, PEG-30 stearate, PEG-40 stearate, PEG-50 stearate and PEG-100 stearate, especially those sold under the name "Myrj" by the company ICI.

fatty acid esters of glycerol, such as glyceryl stearate or oleate or mixtures containing them, especially those sold under the names "Tegin" by the company GOLDSCHMIDT and "Arlacel 165" and "Arlacel 186" by the company ICI, polyethylene glycol ethers of glyceryl fatty acid esters, such as PEG-glyceryl stearate or oleate or laurate, for example the products sold under the name "Arlatone 983S" by the company ICI, polyethoxylated, polypropoxylated or polyglycerolated fatty alcohols possessing a fatty chain containing from 8 to 18 carbon atoms polypropoxylated and polyglycerolated fatty acids, copolymers of ethylene oxide and propylene oxide, polyethoxylated fatty amines or amides, such as PEG-cocamide, PEG-cocamine, PEG-lauramide, PEG-oleamide, PEG-oleamine, PEG-stearamide and PEG-stearamine, fatty esters and ethers of sugars, especially of glucose and sucrose, such as the products sold under the names "Grilloten" by the company RITA and "Grillocose" by the company GRILLOWERKE and "Glucate" and "Glucamate" by the company AMERCHOL, alkyl polyglycosides and mixtures containing them, such as the products sold under the names "Montanov 68" and "Oramix" by the company SEPPIC.

Other surfactants capable of being present in the emulsions according to the invention are:

the condensation products of a monohydric alcohol, an α-diol, an alkylphenyl, an amide or a diglycolamide with glycidol or a precursor of glycidol, especially those corresponding to the formula below:

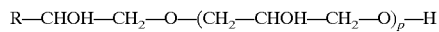

in which R denotes an aliphatic, cycloaliphatic or arylaliphatic radical preferably having between 7 and 21 carbon atoms, it being possible for the aliphatic chains to contain ether, thioether or hydroxymethylene groups, and where p is a statistical value between 1 and 10 inclusive, as are described in French Patent Application FR-A-2,091,516, the compounds corresponding to the formula:

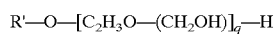

in which R' denotes a $C_8$–$C_{30}$ alkyl, alkenyl or alkylaryl radical and q is a statistical value between 1 and 10 inclusive, as are described in French Patent Application FR-A-1,477,048, the compounds corresponding to the formula:

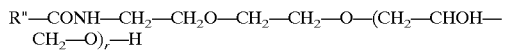

in which R" denotes a saturated or unsaturated, linear or branched aliphatic radical optionally containing one or more hydroxyl groups and having between 8 and 30 carbon atoms, and r represents an integer or decimal number between 1 and 5 (average degree of condensation), as are described in French Patent Application FR-A-2,328,763.

It is also possible, in a well-known manner, for the emulsions according to the present invention to contain co-emulsifiers, whose role is, during the preparation of the initial emulsion (not yet stabilized), to decrease substantially the amount of surfactants needed for production of the said initial emulsion. In this family of products, there may thus be mentioned $C_{14}$–$C_{18}$ fatty alcohols or fatty acids, glyceryl alkyl ethers in which the alkyl chain is a $C_{14}$–$C_{22}$ chain, and also the compounds of formula:

in which $R^1$ and $R^2$, which may be identical or different, represent a cholesteryl, behenyl or 2-octyldodecyl radical.

As particular examples of co-emulsifying agents, there may be mentioned, in particular, stearyl alcohol, cetyl alcohol, stearic acid, chimyl alcohol, betyl alcohol, "Eldew CL-301" marketed by the company AJINOMOTO and sumac wax which contains a mixture of fatty acids.

As stated at the beginning of the description, one of the major advantages of the oil-in-water type emulsions according to the present invention is that these emulsions can contain, while possessing a stable character, active agents, both cosmetic and therapeutic, possessing strongly acidic character, it hence being possible for these active agents to be chosen, in particular, from all those customarily used at present in the field of cosmetics, dermatology or medicinal products.

There may thus be mentioned, inter alia, ascorbic acid, kojic acid, caffeic acid, salicylic acid and its derivatives, alpha-hydroxy acids such as lactic acid, methyllactic acid, glucuronic acid, glycolic acid, pyruvic acid, 2-hydroxybutanoic acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxydodecanoic acid, 2-hydroxytetradecanoic acid, 2-hydroxyhexadecanoic acid, 2-hydroxyoctadecanoic acid, 2-hydroxytetraeicosanoic acid, 2-hydroxyeicosanoic acid, mandelic acid, benzilic acid, phenyllactic acid, gluconic acid, galacturonic acid, citric acid, aleuritic acid, ribonic acid, tartronic acid, tartaric acid, malic acid, fumaric acid, retinoic acid and its derivatives and benzene-1,4-bis(3-methylidene-10-camphorsulfonic acid). The active agents in question can also comprise all natural or synthetic compounds containing such acids, especially plant extracts, and more especially fruit extracts.

As stated above, the compositions for topical use according to the present invention, essentially in the form of acidic O/W type emulsions, may be used in various cosmetic and/or dermatological and/or therapeutic applications, for example in the form of creams for the face, for the body, for the scalp or for the hair, or alternatively in the form of milks for the body or for removing make-up. They can also be used for making up, in particular in the form of make-up foundations, after the addition of pigments to the latter. They can also be used as sun creams after the addition of UV-B and/or UV-A screening agents, or as after-sun creams or milks after the addition of soothing compounds such as panthenol.

The acidic oil-in-water type emulsions intended for stabilization according to the invention may have been obtained according to any technique known per se for the preparation of this type of composition, for example by introducing, with vigorous stirring (the power of the stirring making it possible, in particular, to adjust the size of the particles constituting the fatty disperse phase) and most often in the presence of emulsifying agents, the fatty phase (optionally heated beforehand to increase its fluidity) into an aqueous phase maintained at a temperature generally of between 70 and 80° C., the possible hydrophilic or lipophilic additives, active or otherwise, being capable of being either initially present in the aqueous and/or oily phases, respectively, to be mixed, or added separately during the actual synthesis of the emulsion or after this synthesis. It will be noted that, in the context of the present invention, the mode of preparation of the initial emulsion does not, in fact, assume any critical character.

The method of stabilization of the emulsion as prepared above then involves simply introducing into the emulsion, in a final step, the stabilizing agent (copolymer) according to the present invention.

Other features of the invention will become apparent in the course of the following descriptions of exemplary embodiments which are given for illustration of the invention and are not intended to be limiting thereof.

EXAMPLES

The common procedure which was adopted for preparing these compositions was as follows:

The fatty phase (A) was poured into the aqueous phase (B), which was heated beforehand and maintained at a temperature of between 70 and 75° C., the addition being carried out with vigorous stirring performed by means of a MORITZ type turbo-mixer: when the desired fineness for the emulsion was attained, the medium was cooled to 35–40° C. while stirring using a paddle stirrer; when the latter temperature was reached, acidic active agents (C) were added to the emulsion while stirring using the turbo-mixer; and lastly, the emulsion thereby obtained was stabilized by introducing into it a stabilizing agent according to the invention (D) and which, for all the examples, corresponded to the product as prepared in Example 1 of European Patent Application EP-A-0,503,853 already cited, that is to say a product taking the form of a water-in-oil type emulsion containing approximately 40% by weight of an acrylamide (60 mol %)/AMPS sodium salt (40 mol %)/methylenebisacrylamide (0.22 mmol/mole) crosslinked copolymer, and approximately 4% by weight of an ethoxylated fatty alcohol having an HLB of approximately 12.5.

In all the examples which follow, the compositions are defined in % by weight.

Example 1

This example illustrates the preparation of a moisturizing body milk having a pH of 2.8, based on an O/W emulsion according to the invention.

| Phase A: | |
|---|---|
| Polysorbate 60 ("Tween 60") | 0.8 |
| Perfume | 0.3 |
| Glyceryl stearate and PEG-100 stearate ("Arlacel 165") | 1.0 |
| Hydrogenated polyisobutene | 10 |
| Stearic acid | 1.0 |
| Phase B: | |
| Methylparaben | 0.2 |
| Glycerol | 3.0 |
| Water qs | 100 |
| Phase C: | |
| malic acid | 1.0 |
| Lactic acid | 1.0 |
| Tartaric acid | 1.0 |
| Phase D: | 1.0 |

The composition obtained is completely stable.

Example 2

This example illustrates the preparation and obtaining of a care cream having a pH of 2.2, based on an O/W emulsion according to the invention.

| Phase A: | |
|---|---|
| PEG-20 stearate ("Myrj 49") | 1.0 |
| Glyceryl stearate and PEG-100 stearate ("Arlacel 165") | 1.0 |
| Stearic acid | 1.0 |
| Stearyl alcohol | 2.0 |
| Sesame oil | 10 |
| Hydrogenated isobutene | 10 |
| Perfume | 0.3 |
| Phase B: | |
| Methylparaben | 0.2 |
| Glycerol | 3.0 |
| Soya bean protein hydrolysate | 0.2 |
| Water qs | 100 |
| Phase C: | |
| Glycolic acid | 3.0 |
| Phase D: | 1.0 |

The composition obtained is completely stable.

Example 3

This example illustrates the preparation and obtaining of a care fluid for greasy skins, having a pH of 2.8 and based on an O/W emulsion according to the invention.

| Phase A: | |
|---|---|
| Methylglucose sesquistearate ("Glucate SS") | 2.0 |
| Apricot oil | 10 |
| Cyclomethicone | 3.0 |
| Perfume | 0.2 |
| Phase B: | |
| Methylparaben | 0.2 |
| PEG-20 methylglucose sesquistearate ("Glucamate SS E 20") | 2.0 |
| Xanthan gum | 0.2 |
| Water qs | 100 |
| Phase C: | |
| Lactic acid | 3.0 |
| Phase D: | 0.8 |

The composition obtained is completely stable.

This application is based on French Patent Application No. 93–10966, filed on Sep. 15, 1993, which is incorporated herein in its entirety by reference.

Obviously, numerous modifications and variations of the present invention are possible in light of the above teachings. It is therefore to be understood that, within the scope of the appended claims, the invention may be practiced otherwise than specifically described herein.

What is claimed as new and desired to be secured by Letters Patent of the United States is:

1. A method for preparing an oil-in-water emulsion having a pH of 3 or below, comprising combining the following:
   a) an oily phase;
   b) an aqueous phase;
   c) an acid; and
   d) a polyacrylamide copolymer comprising polymerized units of acrylamide and 2-acrylamido-2-methylpropanesulfonic acid or salt thereof and crosslinked with at least one crosslinking agent possessing, in monomer form, multiple olefinic unsaturation;
   wherein, when combined, said oily phase (a) is dispersed in said aqueous phase (b), said oil-in-water emulsion has a pH of 3 or below, and wherein said acid is selected from the group consisting of ascorbic acid, kojic acid, caffeic acid, salicylic acid, lactic acid, methyllactic acid, glucuronic acid, glycolic acid, pyruvic acid, 2-hydroxybutanoic acid, 2-hydroxypentanoic acid, 2-hydroxyhexanoic acid, mandelic acid, benzylic acid, phenyllactic acid, gluconic acid, galactauronic acid, citric acid, aleuritic acid, tartronic acid, tartaric acid, malic acid, fumaric acid, benzene-1,4-bis(3-methylidene-10-camphorsulfonic) acid, mixtures thereof, and plant and fruit extracts containing said acids.

2. The method of claim 1, wherein said crosslinking agent is present in said copolymer in an amount of between 0.06 and 1 mmol per mole based on total monomer units present in the crosslinked polyacrylamide copolymer.

3. The method of claim 1, wherein said polyacrylamide copolymer comprises polymerized acrylamide units and polymerized acrylamide-2-methylpropanesulfonic acid or salt thereof units in a ratio of from 85:15–15:85.

4. The method of claim 1, wherein said polyacrylamide copolymer comprises polymerized acrylamide units and polymerized acrylamide-2-methylpropanesulfonic acid or salt thereof units in a ratio of from 70:30–30:70.

5. The method of claim 1, wherein said polyacrylamide copolymer comprises polymerized acrylamide units and polymerized acrylamide-2-methylpropanesulfonic acid or salt thereof units in a ratio of from 65:35–35:65.

6. The method of claim 1, wherein said polyacrylamide copolymer comprises polymerized acrylamide units and polymerized acrylamide-2-methylpropanesulfonic acid or salt thereof units in a ratio of from 60:40–40:60.

7. The method of claim 1, wherein said emulsion comprises polymerized units of 2-acrylamido-2-methylpropanesulfonic acid salt.

8. The method of claim 1, wherein said crosslinking agent possessing, in monomer form, multiple olefinic unsaturation, is selected from the group consisting of crosslinked methylenebisacrylamide, crosslinked allylsucrose and crosslinked pentaerythritol.

9. The method of claim 1, wherein said copolymer is present in an amount of from 0.01–5% by weight based on the total weight of the emulsion.

10. The method of claim 1, wherein said copolymer is present in an amount of from 0.1–3% by weight based on the total weight of the emulsion.

11. The method of claim 2, wherein said copolymer is present in an amount of from 0.01–5% by weight based on the total weight of the emulsion.

12. The method of claim 1, further comprising combining the emulsion with a cosmetically-acceptable carrier.

13. The method of claim 11, further comprising combining the emulsion with a cosmetically-acceptable carrier.

14. The method of claim 1, wherein said emulsion comprises isoparaffin.

15. The method of claim 11, wherein said emulsion comprises isoparaffin.

16. The method of claim 1, wherein said emulsion comprises a silicone oil.

17. The method of claim 15, wherein said emulsion comprises a silicone oil.

18. The method of claim 1, wherein said emulsion comprises isoparaffin and a silicone oil.

19. The method of claim 1, wherein said emulsion comprises salicylic acid.

20. The method of claim 17, wherein said emulsion comprises salicylic acid.

21. The method of claim 18, wherein said emulsion comprises salicylic acid.

22. The method of claim 21, wherein said emulsion comprises at least one member selected from the group consisting of stearyl alcohol, cetyl alcohol, steric acid, chimyl alcohol, betyl alcohol and sumac wax.

23. A method for preparing a stabilized oil-in-water emulsion having a pH of 3 or below and comprising:
   adding a polyacrylamide copolymer to an initial acidic emulsion having a pH of 3 or below, comprising:
   a) an oily phase;
   b) an aqueous phase; and
   c) an acid;
   wherein said polyacrylamide copolymer comprises polymerized units of acrylamide and 2-acrylamido-2-methylpropanesulfonic acid or salt thereof and is crosslinked with at least one crosslinking agent possessing, in monomer form, multiple olefinic unsaturation;
   wherein, when combined, said oily phase (a) is dispersed in said aqueous phase (b), said stabilized oil-in-water emulsion has a pH of 3 or below, and wherein
   said acid is selected from the group consisting of ascorbic acid, kojic acid, caffeic acid, salicylic acid, lactic acid, methyllactic acid, glucuronic acid, glycolic acid, pyruvic acid, 2-hydroxybutanoic acid, 2-hydroxypentanoic acid, 2-hydroxyhexanoic acid, mandelic acid, benzylic acid, phenyllactic acid, gluconic acid, galactauronic acid, citric acid, aleuritic acid, tartronic acid, tartaric acid, malic acid, fumaric acid, benzene-1,4-bis(3-methylidene-10-camphorsulfonic) acid, mixtures thereof, and plant and fruit extracts containing said acids.

24. The method of claim 23, wherein said crosslinking agent is present in said copolymer in an amount of between 0.06 and 1 mmol per mole based on total monomer units present in the crosslinked polyacrylamide copolymer.

25. The method of claim 23, wherein said crosslinking agent possessing, in monomer form, multiple olefinic unsaturation, is selected from the group consisting of crosslinked methylenebisacrylamide, crosslinked allylsucrose and crosslinked pentaerythritol.

26. The method of claim 23, wherein said copolymer is present in an amount of from 0.01–5% by weight based on the total weight of the stabilized oil-in-water emulsion.

27. The method of claim 23, wherein said stabilized oil-in-water emulsion comprises isoparaffin.

28. The method of claim 23, wherein said stabilized oil-in-water emulsion comprises a silicone oil.

29. The method of claim 23, wherein said stabilized oil-in-water emulsion comprises isoparafflin and a silicone oil.

30. The method of claim 23, wherein said stabilized oil-in-water emulsion comprises salicylic acid.

31. The method of claim 23, wherein said stabilized oil-in-water emulsion comprises isoparaffin, silicone oil, salicylic acid and at least one member selected from the group consisting of stearyl alcohol, cetyl alcohol, steric acid, chimyl alcohol, betyl alcohol and sumac wax.

* * * * *

UNITED STATES PATENT AND TRADEMARK OFFICE
CERTIFICATE OF CORRECTION

PATENT NO. : 6,001,379

DATED : December 14, 1999

INVENTOR(S): Jacqueline Griat

It is certified that an error appears in the above-identified patent and that said Letters Patent is hereby corrected as shown below:

On the title page and in Column 1, Item [60], the Related US Application Data is incorrectly listed. Item [60] should read as follows:

Continuation of application No.08/621,344, Mar. 25, 1996, Pat. No. 5,863,545, which is a division of application No. 08/305,912, Sep. 15, 1994, Pat. No. 5,531,993.

Signed and Sealed this

Seventeenth Day of April, 2001

*Attest:*

NICHOLAS P. GODICI

*Attesting Officer*  *Acting Director of the United States Patent and Trademark Office*